United States Patent [19]

Lekholm

[11] Patent Number: 5,029,582
[45] Date of Patent: Jul. 9, 1991

[54] MEDICAL APPARATUS FOR STIMULATING A PHYSIOLOGICAL EVENT IN A PATIENT WITH A STIMULATION INTENSITY AUTOMATICALLY ADAPTED TO THE PHYSICAL ACTIVITY OF THE PATIENT AND A METHOD FOR ADAPTING THE STIMULATION INTENSITY TO THE PHYSICAL ACTIVITY OF THE PATIENT

[75] Inventor: Anders Lekholm, Bromma, Sweden

[73] Assignee: Siemens Aktiengesellschaft, Munich, Fed. Rep. of Germany

[21] Appl. No.: 478,228

[22] Filed: Feb. 9, 1990

[30] Foreign Application Priority Data

Feb. 10, 1989 [EP] European Pat. Off. ........... 89102347

[51] Int. Cl.⁵ ............................................. A61N 1/365
[52] U.S. Cl. ............................... 128/419 PG; 128/736
[58] Field of Search .................... 128/419 PG, 736

[56] References Cited

U.S. PATENT DOCUMENTS 4,543,954 10/1985 Cook et al. .................... 128/419 PG
4,722,342 2/1988 Amundson .................... 128/419 PG
4,803,987 2/1989 Calfee et al. ................. 128/419 PG

FOREIGN PATENT DOCUMENTS

0222681 9/1986 European Pat. Off. .
0229886 10/1986 European Pat. Off. .

Primary Examiner—William E. Kamm
Attorney, Agent, or Firm—Hill, Van Santen, Steadman & Simpson

[57] ABSTRACT

A medical apparatus for stimulating a physiological event in a patient, with the stimulation intensity being automatically adapted to the physical activity of the patient, includes respective sensors for monitoring the chronological curves of the temperature within the patient and at the body periphery of the patient. These temperature curves are used as a basis for determining the activity level of the patient, and for setting the stimulation intensity in accordance with that physical activity.

34 Claims, 4 Drawing Sheets

MEDICAL APPARATUS FOR STIMULATING A PHYSIOLOGICAL EVENT IN A PATIENT WITH A STIMULATION INTENSITY AUTOMATICALLY ADAPTED TO THE PHYSICAL ACTIVITY OF THE PATIENT AND A METHOD FOR ADAPTING THE STIMULATION INTENSITY TO THE PHYSICAL ACTIVITY OF THE PATIENT

BACKGROUND OF THE INVENTION

1. Field of the Invention

The present invention is directed to a medical apparatus, such as a heart pacemaker, for stimulating a physiological event in a patient, and in particular to such an apparatus wherein the stimulation intensity is automatically adapted to the physical activity of the patient. A method for adapting the stimulation intensity to the physical activity is also disclosed.

2. Description of the Prior Art

A heart pacemaker is known from European Application 0 232 681 wherein the frequency at which a stimulation pulses are supplied to the heart of the pacemaker user is adjustable on the basis of the physical activity of the pacemaker user. The adaptation of the stimulation frequency at the beginning of physical activity is made on the basis of the difference between the temperature present in the interior of the patient and the temperature present in the region of the body periphery of the patient. For extended physical activity, the adaptation of the stimulation frequency is undertaken in a different manner, for example, with reference only to the temperature present in the interior of the patient.

A difference between the temperature in the interior of the body (i.e., in the body core) and the temperature in the region of the body periphery, with certain known exceptions, is always present. Changes in this temperature difference, however, need not necessarily be related to a change in the physical activity of the patient. There is the risk in the case in the aforementioned known heart pacemaker that the stimulation frequency will be altered without a corresponding change in the physical activity level being present. This need not necessarily represent a risk for the patient in whom the heart pacemaker is implanted, but will at least produce discomfort. A change in the temperature present in the interior of the body, such as the blood temperature, which is used in this know heart pacemaker for adapting the stimulation frequency to extended physical activity, also need not necessarily be based on a modified physical activity of the patient, so that the risk of mismatching the stimulation frequency to the current physical activity is present.

SUMMARY OF THE INVENTION

It is an object of the present invention to provide an apparatus for stimulating a physiological event in a patient wherein the stimulation intensity is reliably adapted to the physical activity of the user of the apparatus.

It is a further object of the present invention to provide such an apparatus wherein a reliable distinction can be made as to whether a change in the body temperature of the user of the apparatus is the result of a change in the physical activity level of the patient, or in caused by something else.

It is a further object of the present invention to provide a reliable method for adapting the stimulation intensity of such an apparatus to the body activity of the user of the apparatus.

These and other objects are achieved in a method and apparatus wherein means for setting the stimulation intensity are provided which take the chronological curves of the respective temperatures at the body periphery and inside the body into consideration. If static conditions are present, the temperature in the interior of the patient will generally lie above the temperature at the region of the body periphery. If, proceeding from a static condition, the physical activity level of the patient increases, both the temperature in the interior of the patient and the temperature in the region of the body periphery will increase. Because body tissue has a high specific heat and a low thermal conductivity, a temperature increase caused by increasing physical activity of the patient will generally appear earlier in the interior of the patient, as a consequence of the dissipated heat arising in the patient's muscles, than will a corresponding rise in the temperature in the region of the body periphery. Conversely, if the patient moves, for example, from a cold room into a warm room, an increase of the temperature in the region of the body periphery will occur first, and a corresponding increase in the temperature in the interior of the body will occur with a chronological delay. The chronological sequence in which changes in the curves of the respective temperatures occur thus permits the "flow direction" of the heat to be recognized, and is thus an indicator of whether the change in the body temperature is to be attributed to a heat source inside the body of the patient (physical activity) or outside of the body of the patient (for example, high room temperature). The stimulation apparatus disclosed herein is thus capable of identifying whether a change in the body temperature is based on a change in the physical activity level of the patient or is caused by something else, and the means for setting the stimulation intensity is adjusted only when there is a reason to do so based on the physical activity level of the patient. Such a differentiated control of the means for setting the stimulation intensity is achieved in a first embodiment of the apparatus wherein the operational sign of the slope of the chronological curve of at least one of the interior or body periphery temperatures is used as a basis for altering the stimulation intensity.

In a further embodiment of the invention, the means for setting the stimulation intensity uses the operational sign of the slope of at least one of the chronological temperature curves, and also uses the chronological curve of the difference between the two temperatures as a basis for altering the stimulation intensity. The difference curve is analyzed to determine the occurrence of an upward or downward transgression of a normal difference value. This type of analysis also permits a determination to be made as to whether the "heat flow" occurs from the interior of the body to the exterior, or vice versa.

In both embodiments, the most recently occurring change in the parameter under consideration is used given the appearance of a static condition of the temperatures. In both embodiments, one of the two temperatures, particularly the temperature in the interior of the patient, is preferably used as a measure for the intensity of the physical activity of the patient. The advantage of both embodiments is that the direction of the "heat flow" is identified in the case of the change in the body temperature, as a result of which the apparatus can determine whether a change, particularly an increase, in the body temperature of the patient is due to an increase in the physical activity level of the patient, or is the result of some other source.

A further differentiation in the causes of changes in the body temperature is possible in a modification applicable to both embodiments wherein the means for setting the stimulation intensity also takes into consideration the magnitude of the slope of the chronological curve of at least one of the temperatures. In a further modification, the means for setting the stimulation intensity can make use of the operational sign of the slopes of both of the respective chronological curves for the temperatures.

In a preferred embodiment, the apparatus is a heart pacemaker, and the physiological event which is stimulated is an atrial and/or ventricular contraction of the heart muscle of the patient. The pacemaker may be of the type known as a demand pacemaker, wherein generation of artificial stimulation pulses occurs only in the absence of natural of spontaneous heart activity, i.e., only as needed by the patient.

The method disclosed herein is a method for reliably correlating the stimulation intensity in such an apparatus to changes in the level of the physical activity of a user of the apparatus by undertaking measurement of the temperature at the body periphery of the user and in the interior, i.e., in the body core, of the user. The method in a first embodiment includes the step of using the operational sign of the slope of the chronological curve of at least one of the temperatures as the basis for altering the stimulation intensity.

A further embodiment of the method includes the additional step of forming a chronological curve which represents the difference between the two temperatures, and using the occurrence of an upward or downward transgression by this chronological difference curve of a normal difference value as a basis for altering the stimulation intensity, in combination with the operational sign of the slope of one of the chronological temperature curves.

As in the apparatus, the accuracy with which the stimulation intensity is varied can be furthered improved by the additional step of using the magnitude of the slope of at least one of the temperature curves as a further basis for altering the stimulation intensity. Further refinement can be obtained by using the operational sign of both of the temperature curves in the method.

As used herein, the term "stimulation intensity," is intended as a comprehensive term which includes one or more of the duration, frequency or repetition rate, amplitude, etc. with which the stimulation means are activated The term "stimulation intensity" also encompasses the pacing mode of stimulation, such as dual chamber DDD, DDI, VDD or VVIR pacing, single chamber pacing, as well as automatic changes of pacing parameters such as the duration of the refractory period, the AV interval, PMT (pacemaker-mediated tachycardia) prevention, etc. These characteristics and/or modalities can be modified alone or in combination to result collectively in a change in the stimulation intensity.

DESCRIPTION OF THE PREFERRED EMBODIMENTS

Figure 1:
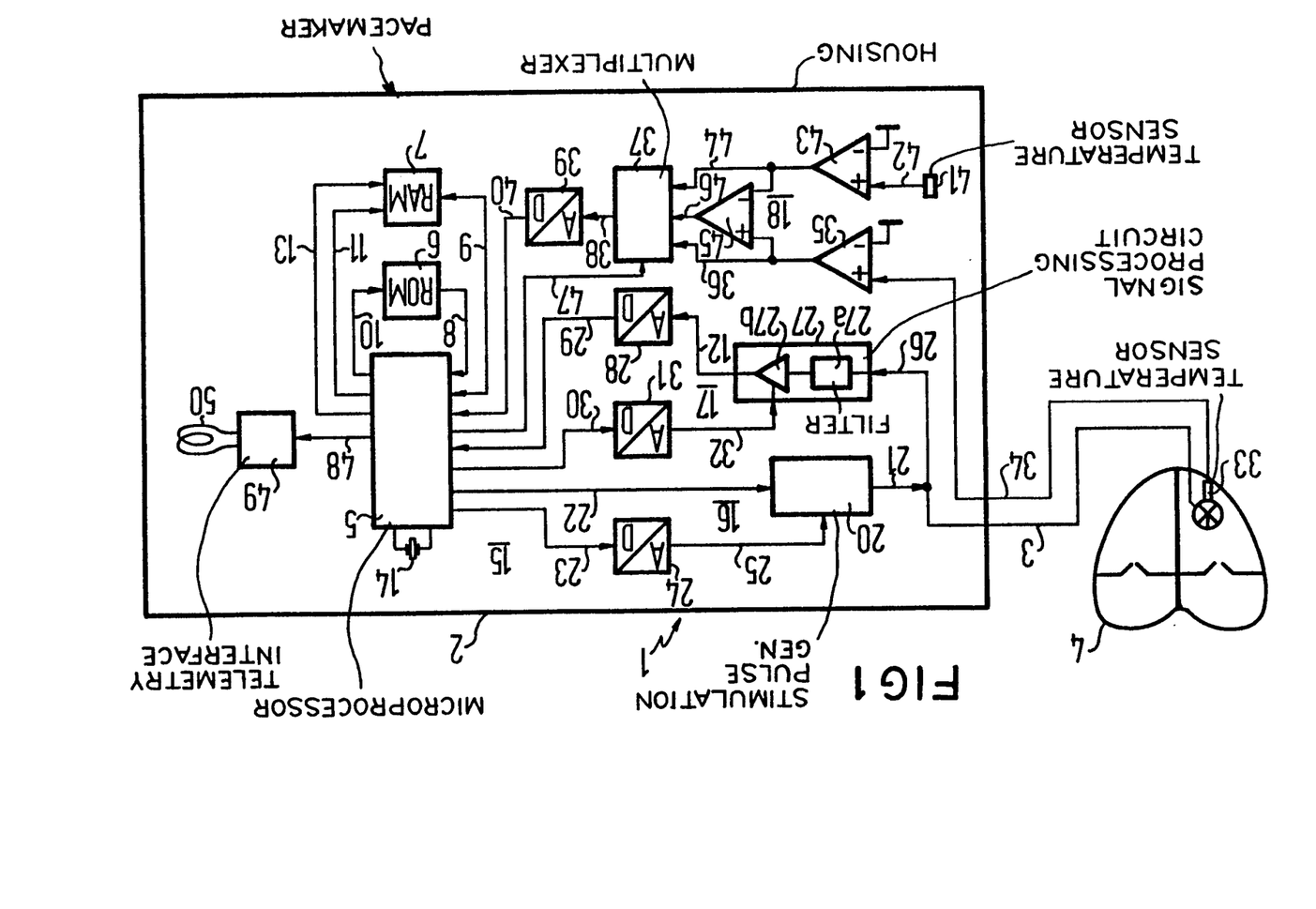
FIG. 1 is a schematic block diagram of a first embodiment of a medical stimulation apparatus, in particular a heart pacemaker, constructed and operating in accordance with the principles of the present invention.

A first embodiment of a medical stimulation apparatus constructed and operating in accordance with the principles of the present invention is shown in FIG. 1. As an example, the stimulation apparatus is a heart pacemaker 1. The pacemaker 1 has a housing 2 in which the various internal components are hermetically sealed. A lead 3 extends from the housing 2 to a heart 4 of a patient, and terminates and is anchored in the right ventricle. The pacemaker 1 may thus be operated in the VVI mode.

Figure 5:
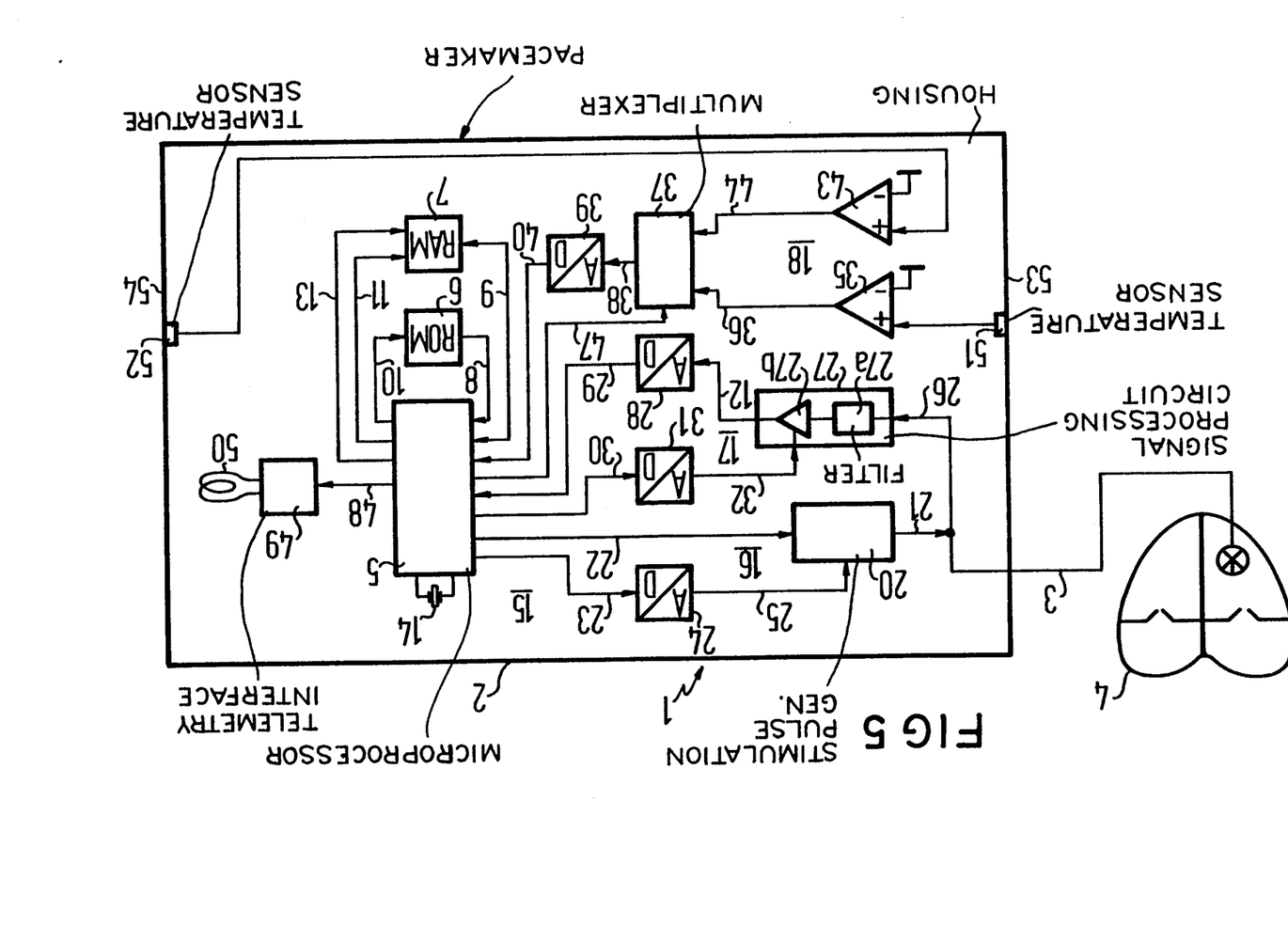
FIG. 5 is a schematic block diagram of a further embodiment of a medical stimulation apparatus, such as a heart pacemaker, constructed and operating in accordance with the principles of the present invention.

Only components necessary for an explanation of the method and apparatus disclosed herein ar shown in FIG. 1 (and FIG. 5). Inter alia the pacemaker 1 includes a microprocessor 5 to which a read only memory (ROM) 6 and a read-write memory (RAM) 7 are allocated. The ROM 6 is in communication with the microprocessor 5 via a data line 8 and an address line 10, and the RAM 7 is in communication with the microprocessor 5 via a data line 9 and an address line 11. A line 13 is provided from the microprocessor to the RAM 7 which switches the RAM 7 from a write mode to a read mode, and vice versa. A program with which all functions of the pacemaker 1 are controlled is stored in the ROM 6. When it is stated below that the microprocessor 5 executes a specific function, this is understood to mean that the microprocessor 5 is activated for the execution of that function by the execution of the program stored in the ROM 6 using the data stored in the RAM 7 and data supplied to the microprocessor 5 in some other manner, for example by an input wiring.

A crystal 14 is connected to the microprocessor 5 for generating clock signals and supplying those signals to the microprocessor 5. The crystal 14 also constitutes the time reference for the operation of the pacemaker 1.

The microprocessor has I/0 lines referenced 15 generally, and has channels generally referenced 16, 17 and 18.

The channel 16 supplies the heart 4 with stimulation pulses as required. The channel 16 thus includes a stimulation pulse generator 20 having an output line connected to the lead 3. The stimulation pulse generator 20 may be activated via a line 22 connected to an output of the microprocessor 5 to generate a stimulation pulse. Digital data relating to the energy content of the stimulation pulses, for example amplitude and/or duration, proceed from the microprocessor 5 via a line 23 to a digital/analog interface 24, which supplies the stimulation pulse generator 20 with analog control signals corresponding to the digital data. These control signals are supplied via a control line 25 and set the stimulation pulse generator 20 so that it generates stimulation pulses having the desired energy content, as needed.

The channel 17 includes a signal processing circuit 27 also connected to the lead 3, via an input line 26. The signal processing circuit 27 filters and amplifies an electrical signal which is obtained from the heart 4 via the lead 3, and which corresponds to the activity of the heart. The signal processing circuit 27 includes a filter 27a and an amplifier 27b. The processed signal proceeds from the output of the signal processing circuit 27 to an analog-to-digital converter 28 via a line 12. Digital data proceed from the converter 28 via a line 29 to a corresponding input of the microprocessor 5. The digital data correspond to the curve of the electrical signal at the output of the signal processing circuit 27, which in turn reflects the electrical activity of the heart 4. The microprocessor 5 has a line 30 leading to a digital/analog interface 31 which forwards digital data supplied thereto by the microprocessor 5 to the signal processing circuit 27 as corresponding analog signals via a control line 32. The digital data, or the corresponding analog signals, function, for example, to set the gain of the amplifier 27b, or may completely inhibit the amplifier 27b.

The digital data supplied via the line 29 to the microprocessor 5 are analyzed by the microprocessor 5 to determine whether electrical activity corresponding to the appearance of a natural heartbeat is contained within the electrical signal from the heart 4. If the microprocessor 5 detects the occurrence of a natural heartbeat, or when it activates the generation of a stimulation pulse by the stimulation pulse generator 20, the microprocessor 5 begins to operate as a counter, and counts a plurality of clock pulses received from the crystal 14 which correspond to a time interval adjustable between an upper and lower limit. The time interval which is set in this manner defines the stimulation frequency with which the heart 4 is stimulated in the absence of natural heartbeats. If no data which the microprocessor 5 interprets as a natural heartbeat are received via the channel 17 during a time interval corresponding to the desired heartbeat rate, the microprocessor 5 activates the stimulation pulse generator 20 after expiration of the time interval. Following the generation of a stimulation pulse by the pulse generator 20, the microprocessor 5 again begins to count a plurality of clock pulses, which correspond to the time interval which has been set and which defines the stimulation frequency. If, by contrast, the microprocessor 5 detects a natural heartbeat during this time interval, it aborts the counting process as long as a further time interval, known as the refractory time, has expired, and begins the counting process anew.

The time interval defining the stimulation frequency is adjustable between, for example, 400 and 2,000 ms. The refractory time typically lasts between about 250 and 450 ms and is also adjustable. The refractory time is subdivided into an absolute refractory time having a fixed duration of, for example, 125 ms, and into a relative refractory time which contains the remaining part of the total refractory time. The refractory time begins to run simultaneously with the time interval which defines the stimulation frequency, and is identified by the microprocessor 5 in the same counting process which also serves to identify the time interval which defines the stimulation frequency.

The amplifier 27b of the signal processing circuit 27 in the channel 17 is completely inhibited during the absolute refractory time. This is achieved by the microprocessor 5 supplying a control signal to the amplifier 27b via the line 30, the digital/analog interface 31 and the control line 32. As a consequence of the complete inhibiting the of the amplifier 27b no detection whatsoever by the microprocessor 25 is possible for the duration of the absolute refractory time. After the expiration of the absolute refractory time, the microprocessor 5 re-activates the amplifier 27b, so that it is able to detect natural heartbeats. If the microprocessor 5 detects a natural heartbeat during the relative refractory time, it does not abort the counting process for identifying the time interval which defines the stimulation frequency—contrary to the detection of a natural heartbeat after the expiration of the refractory time—but instead continues the counting and concludes the counting with the activation of the stimulation pulse generator 20. After the detection of a natural heartbeat, however, the microprocessor 5 again activates the full refractory time. Stimulation pulses having a stimulation frequency defined by the time interval which has been set are thus generated independently of the appearance of natural heartbeats in the case of, for example, radio-frequency disturbances which may result in a misdetection. Even when the spontaneous heartbeat frequency is so high that the appearance of natural heartbeats ensues every time within the relative refractory time, the generation of stimulation pulses occurs with the stimulation frequency defined by the set time interval until the spontaneous heartbeat frequency has fallen below a frequency having a period corresponding to the refractory time which has been set. Re-entry tachycardia is thus terminated by this function.

The channel 18 supplies the microprocessor 5 with data corresponding to the physical activity of the patient in whom the heart pacemaker 1 has been implanted. The data permit the microprocessor 5 to set the time interval which defines the stimulation frequency in a manner which is adapted to the physical activity of the patient. For this purpose, the lead 3 has its electrode end implanted in the right ventricle of the heart 4 and is provided with a temperature sensor 33 disposed in the interior of the right ventricle. The sensor 33 measures the temperature of venous blood. Because the dissipated energy arising in the muscles of the patient is carried away to a considerable degree by the venous blood, this temperature represents a useable indicator of the physical activity level of the patient. The temperature sensor 33 generates an electrical signal corresponding to the sensed temperature, which proceeds to an operational amplifier via a line 34, proceeding parallel to the stimulation line within the lead 3, and which also enters the housing 2 of the pacemaker 1. The output of the operational amplifier 35 is supplied via a line 36 to one of the inputs of a multiplexer 37, described in greater detail below. The output of the multiplexer 37 is supplied via a line 38 to an analog-to-digital converter 39, which converts the signal into corresponding digital data which are supplied to the microprocessor 5 via a line 40.

On the basis of the digital data, the microprocessor 5 calculates the chronological course of the signal from the temperature sensor 33, and thus calculates the chronological course of the temperature of the venous blood in the right ventricle. Based on this calculation, the microprocessor 5 sets a time interval which defines the stimulation frequency so that stimulation of the heart 4, as needed, ensues with a frequency adapted to the physical activity of a patient. This time interval may be set between an upper and a lower limit. A suitable algorithm for setting the stimulation frequency based on physical activity data is described, for example, in U.S. Pat. No. 4,543,954.

As is known, changes in the body temperature as well as changes in the temperature of the venous blood need not necessarily be caused by a corresponding change in the physical activity level of a patient. If only the temperature of the venous blood were used to control the stimulation intensity, there would thus be the risk that the time interval which defines the stimulation frequency would be altered by the microprocessor 5 based on a change in the temperature measured by the temperature sensor 33 without such a stimulation intensity modification being required in view of the physical activity level of the patient.

To prevent or minimize such a risk, the pacemaker 1 shown in FIG. 1 includes a second temperature sensor 41. This temperature 41 is arranged in the interior of the housing 2 of the pacemaker 1. The temperature sensor 41 is disposed within the housing 2 so that it measures the temperature in the region of the body periphery of the patient in whom the pacemaker 1 has been implanted. This is possible since heart pacemakers are generally implanted between subcutaneous tissue and muscle tissue. The temperature sensor 41 will thus preferably be disposed in the pacemaker housing 2 at a location so that the temperature sensor 41 faces the exterior of the patient when the pacemaker 1 is implanted.

The electrical signal from the temperature sensor 41 proceeds via a line 42 to an operational amplifier 43. The output of the amplifier 43 is supplied to the multiplexer 37 via a line 44. The output signals of the amplifiers 35 and 43 also proceed respectively to the inverting and non-inverting inputs of a differential amplifier 45, which forms a signal corresponding to the difference between the temperatures measured by the temperature sensors 33 and 41. The output of the differential amplifier 45 is supplied via a line 46 to a further input of the multiplexer 37. The multiplexer 37 is controlled by the microprocessor 5 via a clock line 47 so that the multiplexer 37 successively supplies the output signals of the operational amplifier 35, the differential amplifier 45 and the operational amplifier 43 to the analog-to-digital converter 39, which forwards the corresponding digital data to the microprocessor 5 via the line 40.

In addition to measuring the chronological course of the temperature measured by the temperature sensor 33, the microprocessor, 5 analyzes the chronological course of the temperature measured by the temperature sensor 41, as well as the difference between these two temperatures. Although in the embodiment of FIG. 1 the differential amplifier 45 has been provided to obtain the difference signal, it would also be possible to calculate such a difference signal within the microprocessor 5, in which case the differential amplifier 43 could be omitted.

In addition to calculating the chronological course of the two temperature signals from the respective sensors 33 and 43, the microprocessor 5 calculates the chronological course of the corresponding slopes in terms of magnitude and operational sign. The microprocessor 5 analyzes, as a function of time, whether the difference upwardly or downwardly exceeds a normal value of the difference. Additionally, the microprocessor 5 calculates the magnitude of the difference between the two temperatures as a function of time, and also calculates the slope of the difference in terms of magnitude and operational sign.

Figure 2:
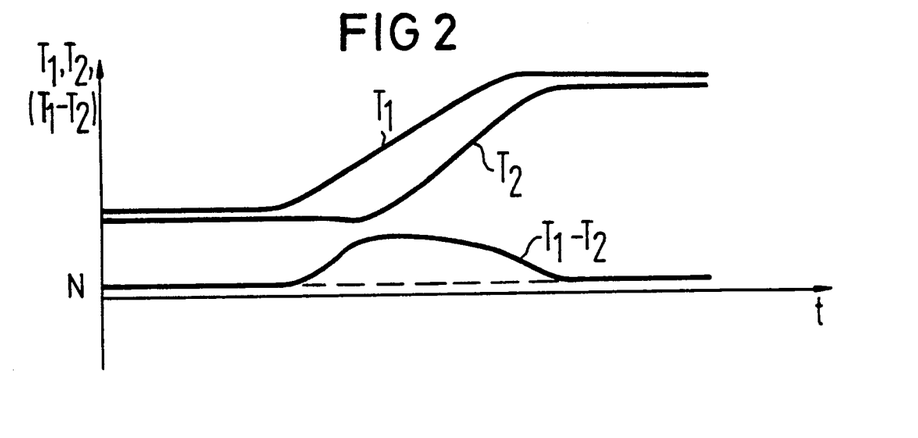
FIGS. 2, 3 and 4 are graphs of curves for explaining the operation of the apparatus of FIG. 1.
Figure 3:
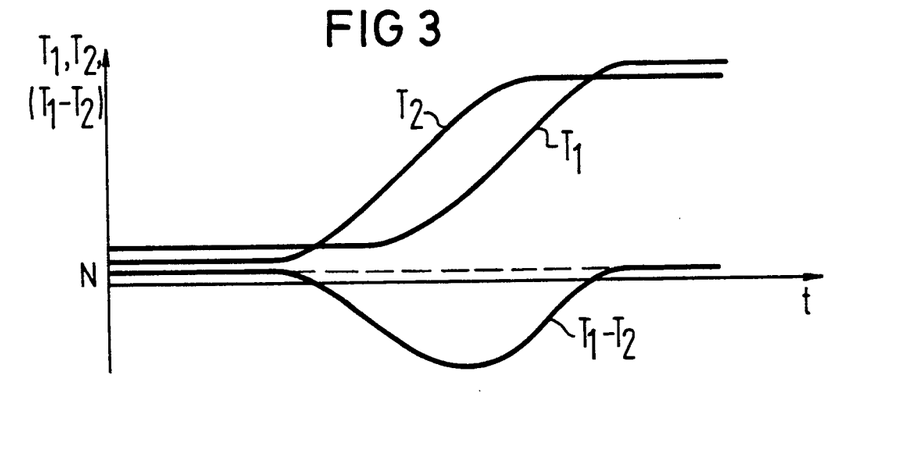
Figure 4:
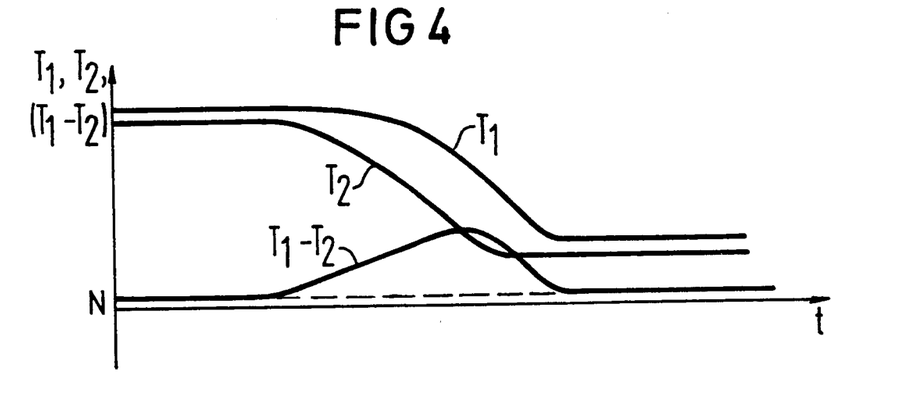

The microprocessor 5 can thus recognize whether a change, such as an elevation in the temperature in the interior of the patient identified by the temperature sensor 33, results from a change, such as an increase, in the physical activity level of the patient, and consequently requires a corresponding adaptation of the stimulation frequency (or of the time interval which defines the stimulation frequency). The microprocessor 5 recognizes this by reference to the operational sign of the slope of the chronological course of one of the two temperatures, for example the temperature present in the interior of the patient. This can also be recognized by determining whether the difference between the two temperatures upwardly or downwardly transgresses a normal value, which is present given static conditions with respect to the temperatures. This is shown in the graphs of FIGS. 2, 3, and 4. Each of the graphs in those respective figures show the courses of the temperatures measured by the respective temperature sensors 33 and 41 over a time span on the order of magnitude of 15 through 60 minutes. The temperature curves referenced $T_1$ correspond to the temperature in the interior of the patient measured by the temperature sensor 33. The temperature curves referenced $T_2$ correspond to the temperature in the region of the body periphery measured by the temperature sensor 41. The illustrated fluctuations in the temperatures $T_1$ and $T_2$ are on the order of magnitude of 1° K. The chronological curve of the difference between the temperatures $T_1-T_2$ is also shown in FIGS. 2 through 4. The maximum values of the difference $T_1-T_2$ are on the order of magnitude of a few tenths of a degree K.

FIGS. 2 shows the conditions which occur when, proceeding from a static condition, an increase in the physical activity level of the patient occurs. In this case, heat is produced in the interior of the patient. This effect is further intensified in that heated blood from the working muscles is pumped to the heart of the patient in the center of the chest cavity. A rise in the temperature $T_1$ which is present in the interior of the patient therefore occurs first without the temperature $T_2$ is the region of the body periphery changing. An increase in the temperature $T_2$ occurs only after a delay time, after which a new equilibrium is established in the physical activity continues. The difference between the temperatures $T_1-T_2$ has a normal or nominal value N, which is relatively small, both before the increase in the physical activity level and after the new equilibrium has been established. During the chronologically offset rises in the temperatures $T_1$ and $T_2$, however, the temperature difference $T_1-T_2$ increases relatively greatly, and thereby upwardly transgresses the normal value N.

It can thus be seen that the operational sign of the slope for each chronological course of the respective temperatures $T_1$ and $T_2$ is positive given an increase in the physical activity level and that the temperature difference $T_1-T_2$ exceeds its normal value N during the increase in physical activity level.

FIG. 3 shows the conditions which arise when the temperature in the environment of the patient increases. This may occur, for example, if the patient moves from a cold room into a warmer room, takes a hot bath, or puts on warm clothing.

In this case, a rise in the temperature $T_2$ in the region of the body periphery occurs first, as a consequence of the application of heat proceeding from the exterior of the patient. This rise is followed by a later rise in the temperature $T_1$ in the interior of the patient. As in the case of an increase in the physical activity level, a rise in the temperatures $T_1$ and $T_2$ also occurs in the case of an increase in the temperature of the environment of the patient. This means that the slopes of the chronological curves of the temperatures $T_1$ and $T_2$ also have a positive operational sign. In contrast to an increase in the physical activity level, however, the temperature difference $T_1-T_2$ falls below the normal value N, and may even assume negative values in the case of an increase in the temperature of the patient's environment.

The new temperature equilibrium which is established in the case of an environmental temperature increase will depend upon the environmental conditions causing the temperature increase. In the case of a hot bath, for example, it is possible that only the respiration system is available as a cooling mechanism for the body of the patient, and thus the difference between the temperatures $T_1-T_2$ will still fall below the normal value N or may still have a negative value after a longer duration.

The conditions shown in FIG. 4 show the result of a rapid cooling of the body of the patient as occurs, for example, in the case of a cold bath. In this case, the temperature $T_2$ in the region of the body periphery of the patient decreases first, before a decrease in the temperature $T_1$ in the interior of the patient occurs. As in the case of an increase in the physical activity of the patient, the difference between the temperature $T_1-T_2$ which occurs exceeds the normal value N. In contrast to the increase in physical activity level and in contrast to an increase in the environment of the patient, the slopes of the respective chronological curves of the temperatures $T_1$ and $T_2$ have negative operational signs under the conditions of FIG. 4.

It is thus clear that the microprocessor 5, by taking the chronological curve of one of the temperatures $T_1$ or $T_2$ in terms of its operational sign and slope into consideration, and by also taking the chronological curve of the difference between the temperatures $T_1-T_2$ into consideration with respect to the upward or downward transgression of the normal value N, is able accurately to adjust the stimulation frequency in view of the modifications of the temperature $T_1$, if the modification of the temperature $T_1$ is in fact caused by a change in the physical activity level of the patient. It is thus insured that an adaptation, particularly an increase in the stimulation frequency, ensues only when a corresponding change in the physical activity of the patient is in fact present, and thus the increase in the stimulation frequency is actually needed.

If the microprocessor 5 also takes into account the magnitude of the slope of the temperature $T_1$ present in the interior of the patient when setting the time interval which defines the stimulation frequency, the accuracy in identifying a change in the physical activity level of the patient can be further improved. The magnitude of the slope of the temperature $T_1$ can be monitored to determine whether the change in the magnitude is sudden or slow. A sudden or rapid change will usually be attributable to a change in the physical activity level of the patient. For similar reasons, the microprocessor takes into account the operational sign of the slopes of the chronological course of both temperatures $T_1$ and $T_2$ and also considers the magnitude of the slope of the chronological curve of the temperature $T_2$ present in the interior of the patient. If a comparison of the chronological curves of the temperatures $T_1$ and $T_2$ implemented by the microprocessor 5, in combination with a change in the physical activity level of the patient, yields considerable differences in the magnitudes of the slopes of the curves for the temperatures $T_1$ and $T_2$, given the same operational sign, or yields different operational signs of the slopes, this is an indication that a considerable change in the temperature of the environment surrounding the patient is occurring simultaneously with the change in the physical activity level of the patient. This may be the case, for example, if the patient begins to swim in cool water. The microprocessor 5 also takes such information into consideration when setting the time interval that defines the stimulation frequency. The microprocessor 5 acquires further information regarding potential temperature changes in the environment of the patient by analyzing the chronological curve of the magnitude of the difference between the temperatures $T_1-T_2$. A negative value for the difference $T_1-T_2$ generally means, for example, that the temperature of the environment of the patient is above the body temperature of the patient. The microprocessor 5 also takes this into consideration when setting time interval that defines the stimulation frequency. As can be seen from FIG. 1, the microprocessor 5 is in communication via a line 48 with a schematically indicated telemetry circuit 59, to which a transmission/reception coil 50 is connected. A bidirectional data stream with an external device, known as a programmer, is possible using the telemetry circuit 49. It is thus possible to call up the variables stored in the RAM 7 for checking those variables or for modifying those variables.

A further embodiment of a heart pacemaker 1 is shown in FIG. 5, wherein components identical to those already described in connection with the pacemaker of FIG. 1 are provided with the same reference characters.

Figure 6:
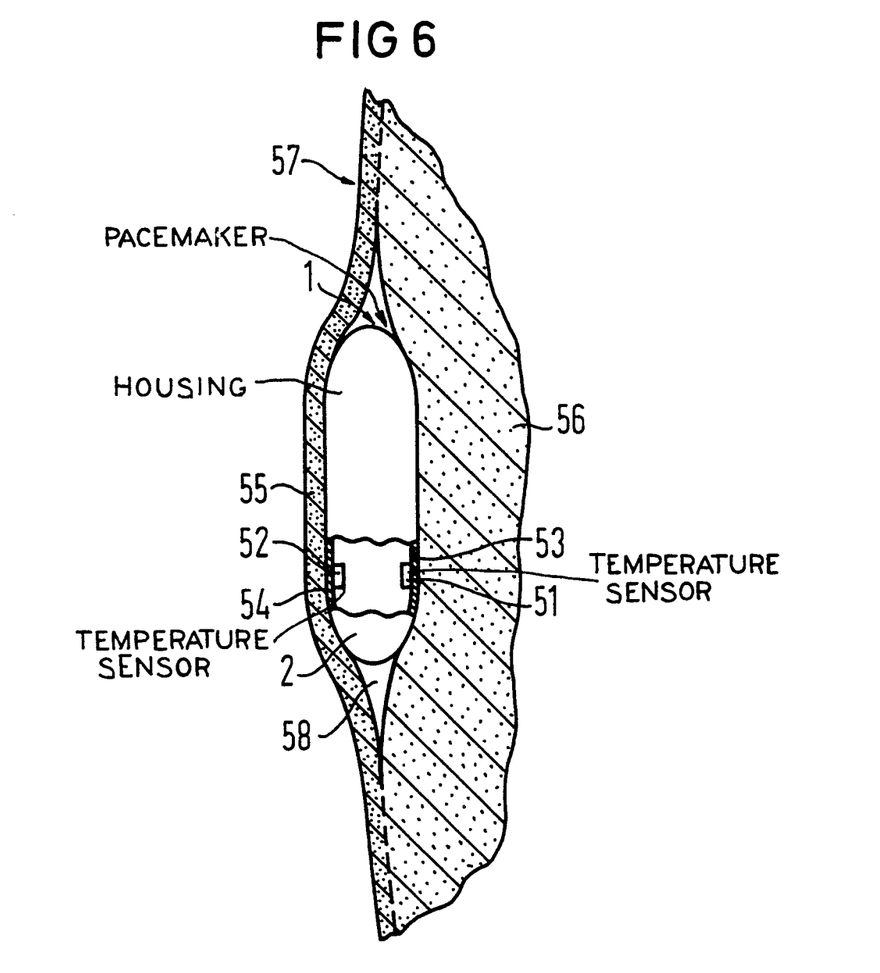
FIG. 6 is a sectional view of a portion of a patient in whom the medical stimulation apparatus has been implanted, showing the location of the temperature sensors.

The main difference between the pacemakers of FIGS. 5 and 1 is that the pacemaker of FIG. 5 has both temperature sensors 51 and 52 arranged in the inside of the housing 2. As schematically shown in FIG. 5, the temperature sensors 51 and 52 are connected to different sections of the inside wall of the housing 2 in heat conducting fashion. This is further illustrated in FIG. 6, wherein only the housing 2 and the temperature sensors 51 and 52 of the heart pacemaker 1 of the FIG. 5 are shown. It can be seen in FIG. 6 that the temperature sensors 51 and 52 are attached to respective wall sections 53 and 54 of the housing 2 which are opposite one another. As can also be seen in FIG. 6, the heart pacemaker 1 is implanted into a pocket 58 situated between the subcutaneous tissue 55 and the muscle tissue 56 of the body 57 of the patient so that the wall section 53, having the temperature 51 attached thereto, faces toward the muscle tissue 56, and thus toward the interior of the body 57 of the patient. The wall section 54 with the temperature sensor 52 attached thereto faces toward the subcutaneous tissue 55, and thus toward the body periphery of the patient. Thus the temperature $T_1$ measured by the temperature sensor 51 corresponds to the temperature in the region of the interior of the patient, and the temperature $T_2$ measured by the temperature sensor 52 corresponds to the temperature in the region of the periphery of the patient. If the housing 2 of the pacemaker 1 consists of material having a low thermal conductivity, for example titanium, the thermal coupling of the temperature sensors 51 and 52 is sufficiently low to avoid disturbing influences on the temperature sensing.

A further difference between the pacemaker 1 of FIG. 5 and the embodiment of FIG. 1 is that the embodiment of FIG. 5 does not include the differential amplifier 45 in the channel 18. As described earlier, the microprocessor 5 can undertake the computational calculation of the difference between the temperatures $T_1$ and $T_2$. In the embodiment of FIG. 5, however, this difference is not primarily considered when setting the time interval which defines the stimulation frequency. Instead, the microprocessor 5 in the embodiment of FIG. 5 analyzes the chronological curves of the temperatures $T_1$ and $T_2$ to determine the chronological sequence of changes in the chronological curves of the two temperatures $T_1$ and $T_2$.

As is clear from the explanation of FIGS. 2 through 4, a change in the temperature $T_1$ present in the interior of the patient occurs first when there is a change, particularly an increase, in the physical activity level of the patient wearing the pacemaker 1. This is followed by a corresponding change in the temperature $T_2$ in the region of the body periphery. If, by contrast, changes in the body temperature of that patient appear which are caused by an external temperature change, for example a warm or cold bath, a change in the temperature $T_2$ in the region of the body periphery occurs first, followed by a corresponding change in the temperature $T_1$ in the interior of the patient.

On the basis of the chronological sequence with which the changes in the temperatures $T_1$ and $T_2$ occur, the microprocessor 5 is thus able to recognize whether these changes are caused by a change in the physical activity level of the patient. Only when this is the case does the microprocessor 5 alter the time interval which defines the stimulation frequency. Further parameters derived from the chronological curves of the temperatures $T_1$ and $T_2$, including the difference between the temperatures $T_1-T_2$, can thus still be considered in the manner described earlier in connection with FIG. 1.

The temperature sensors 33 and 41, or 51 and 52, may, for example, be thermistors or temperature-sensitive semiconductor diodes.

The microprocessor 5, the ROM 6 and the RAM 7 may be combined in a single computer chip in both embodiments.

The functions of the heart pacemakers described in the exemplary embodiments above are controlled by a suitably programmed microprocessor 5. Those functions may, however, also be realized by a conventionally constructed control logic circuit.

Although the embodiments above have been described with reference to heart pacemakers, it will be understood by those skilled in the art that the inventive concept disclosed herein can be employed to advantage in any medical apparatus which stimulates body tissue, wherein it is desireable that a modification in the stimulation intensity occur when the physical activity level of the patient employing the apparatus changes.

Although further modifications and changes may be suggested by those skilled in the art, it is intention of the inventor to embody within the patent warranted hereon all changes and modifications as reasonably and properly come within his scope of his contribution to the art.

I claim as my invention:

1. A medical apparatus implantable in the body of a patient comprising:
    means for stimulating a physiological event in a patient at a stimulation intensity;
    first sensor means for measuring the temperature in the interior of s id patient and generating a first temperature signal corresponding thereto;
    second sensor means for measuring the temperature in the region of the periphery of said patient and generating a second temperature signal corresponding thereto; and
    means connected to said means for stimulating and to said first and second sensor means for modifying said stimulation intensity to adapt said stimulation intensity to the physical activity level of said patient, including means for determining a chronological sequence of changes respectively occurring in said first and second temperature signals for use as a basis for modifying said stimulation intensity.

2. A medical apparatus as claimed in claim 1, wherein each of said first and second temperature signals has a slope having an operational sign, and wherein said means for modifying said stimulation intensity further includes means for identifying the operational sign of the slope of at least one of said first and second temperature signals for use as a further basis for modifying said stimulation intensity.

3. A medical apparatus as claimed in claim 1, wherein each of said first and second temperature signals has a slope having a magnitude, and wherein said means for modifying said stimulation intensity further includes means for identifying the magnitude of the slope of at least one of said first and second temperature signals for use as a further basis for modifying said stimulation intensity.

4. A medical apparatus as claimed in claim 1, wherein each of said first and second temperature signals has a slope having an operational sign, and wherein said means for setting the stimulation frequency includes means for identifying the operational sign of the slope of both said first and second temperature signals for use as a further basis for modifying said stimulation intensity.

5. A medical apparatus as claimed in claim 1, wherein said apparatus is a heart pacemaker, wherein said means for stimulating a physiological event in said patient at a stimulation intensity is a means for stimulating heart activity at a stimulation frequency, and wherein said means for modifying said stimulation intensity is a means for modifying said stimulation frequency.

6. A medical apparatus as claimed in claim 5, wherein said pacemaker has a pacemaker housing, wherein said means for stimulating heart activity includes a lead extending from said housing and terminating in a free end having an electrode adapted for anchoring in the right ventricle of the heart of said patient, wherein said first sensor means includes a first temperature sensor disposed at said free end of said lead for measuring the blood temperature present in the right ventricle, and wherein said second sensor means includes a second temperature sensor mounted in said housing of said pacemaker.

7. A medical apparatus as claimed in claim 1, further comprising:
    a housing having first and second spaced wall sections disposed opposite each other and wherein said housing is adapted for implantation in the body of said patient with said first wall section facing the periphery of said patient and said second wall section facing the interior of said patient, and wherein said first sensor means is mounted at said first wall section and said second sensor means is mounted at said second wall section.

8. A medical apparatus implantable in the body of a patient comprising:

means for stimulating a physiological event in a patient at a stimulation intensity;

first sensor means for measuring the temperature in the interior of said patient and generating a first temperature signal corresponding thereto, said first temperature signal having a slope with an operational sign;

second sensor means for measuring the temperature in the region of the periphery of said patient and generating a second temperature signal corresponding thereto, said second temperature signal having a slope with an operational sign; and means connected to said means for stimulating and to said first and second sensor means for modifying said stimulation intensity to adapt said stimulation intensity to the physical activity level of said patient, including means for identifying the operational sign of the slope of at least one of said first and second temperature signals for use as a basis for modifying said stimulation intensity and including means for determining the difference between said first and second temperature signals and for determining whether said difference upwardly or downwardly transgresses a normal value of said difference for use as a further basis for modifying said stimulation intensity.

9. A medical apparatus as claimed in claim 8, wherein the respective slopes of said first and second temperature signals each have a magnitude, and wherein said means for modifying said stimulation intensity further includes means for identifying the magnitude of the slope of at least one of said first and second temperature signals for use as a further basis for modifying said stimulation intensity.

10. A medical apparatus as claimed in claim 8, wherein said means for setting the stimulation frequency includes means for identifying the operational sign of the slope of both said first and second temperature signals for use in modifying said stimulation intensity.

11. A medical apparatus as claimed in claim 8, wherein said apparatus is a heart pacemaker, wherein said means for stimulating a physiological event in said patient at a stimulation intensity is a means for stimulating heart activity at a stimulation frequency, and wherein said means for modifying said stimulation intensity is a means for modifying said stimulation frequency.

12. A medical apparatus as claimed in claim 11, wherein said pacemaker has a pace maker housing, wherein said means for stimulating heart activity includes a lead extending from said housing and terminating in a free end having an electrode adapted for anchoring in the right ventricle of the heart of said patient, wherein said first sensor means includes a first temperature sensor disposed at said free end of said lead for measuring the blood temperature present in the right ventricle, and wherein said second sensor means includes a second temperature sensor mounted in said housing of said pacemaker.

13. An medical apparatus as claimed in claim 8, further comprising:

a housing having first and second spaced wall sections disposed opposite each other and wherein said housing is adapted for implantation in the body of said patient with said first wall section facing the periphery of said patient and said second wall section facing the interior of said patient, and wherein said first sensor means is mounted at said first wall section and said second sensor means is mounted at said second wall section.

14. A method comprising the steps of:

stimulating a physiological event in a patient at a stimulation intensity;

measuring the temperature in the interior of said patient and generating a first temperature signal corresponding thereto;

measuring the temperature in the region of the periphery of said patient and generating a second temperature signal corresponding thereto;

determining a chronological sequence of changes respectively occurring in said first and second temperature signals; and modifying said stimulation intensity to adapt said stimulation intensity to the physical activity level of the patient based on said chronological sequence of changes.

15. A method as claimed in claim 14, wherein each of said first and second temperature signals has a slope having an operational sign, said method comprising the additional steps of:

identifying the operational sign of the slope of at least one of said first and second temperature signals; and using said operational sign of the slope of said at least one of said first and second temperature signals as a further basis for modifying said stimulation intensity.

16. A method as claimed in claim 14, wherein the said first and second temperature signals each have a slope having a magnitude, and wherein said method further comprises the steps of:

identifying the magnitude of the slope of at least one of said first and second temperature signals; and using said magnitude of the slope of said at least one of said first and second temperature signals as a further basis for modifying said stimulation intensity.

17. A method as claimed in claim 14, wherein each of said first and second temperature signals has a slope having an operational sign, and said method further comprising the identifying the operational sign of the respective slopes of said first and second temperature signals; and using the operational sign of the respective slopes of both of said first and second temperature signals as a further basis for modifying said stimulation intensity.

18. A method comprising the steps of:

stimulating a physiological event in a patient at a stimulation intensity;

measuring the temperature in the interior of said patient and generating a first temperature signal corresponding thereto having a slope with an operational sign;

measuring the temperature in the region of the periphery of said patient and generating a second temperature signal corresponding thereto having a slope with an operational sign;

identifying the operational sign of the slope of at least one of said first and second temperature signals;

forming a difference signal between said first and second temperature signals, said difference signal having a normal value;

determining if said difference signal upwardly or downwardly transgresses said normal value; and modifying said stimulation intensity to adapt to said stimulation intensity to the physical activity level of said patient based on said operational sign of said at least one of said first and second temperature signals and on whether said difference signal upwardly or downwardly transgresses said normal value.

19. A method as claimed in claim 18, wherein the respective slopes of said first and second temperature signals each has a magnitude, and wherein said method further comprises the steps of:

identifying the magnitude of the slope of at least one of said first and second temperature signals; and using said magnitude of the slope of said at least one of said first and second temperature signals as a further basis for modifying said stimulation intensity.

20. A method for pacing a heart comprising the steps of:

stimulating the heart muscle activity in a patient at a stimulation frequency;

measuring the temperature in the interior of said patient and generating a first temperature signal corresponding thereto;

measuring the temperature in the region of the periphery of said patient and generating a second temperature signal corresponding thereto;

determining a chronological sequence of changes respectively occurring in said first and second temperature signals; and modifying said stimulation frequency to adapt said stimulation frequency to the physical activity level of the patient based on said chronological sequence of changes in said first and second temperature signals.

21. A method as claimed in claim 20, wherein the step of stimulating heart activity is further defined as stimulating ventricular contractions in the heart at a stimulation frequency.

22. A method as claimed in claim 20, wherein the step of measuring the temperature in the interior of said patient is further defined as measuring the temperature of the venous blood of said patient.

23. A method as claimed in claim 22, wherein the step of measuring the venous blood of said patient is further defined as measuring the temperature of the venous blood of said patient in the right ventricle.

24. A method as claimed in claim 20, wherein each of said first and second temperature signals has a slope having an operational sign, said method further comprising the steps of:

identifying the operational sign of the slope of at least one of said first and second temperature signals; and using the operational sign of the slope of said at least one of said first and second temperature signals as a further basis for modifying said stimulation frequency.

25. A method as claimed in claim 24, wherein the respective slopes of said first and second temperature signals each has a magnitude, and wherein said method further comprises the steps of:

identifying the magnitude of the slope of at least one of said first and second temperature signals; and using said magnitude of the slope of said at least one of said first and second temperature signals as a further basis for modifying said stimulation intensity.

26. A method for pacing a heart comprising the steps of:

stimulating heart activity in a patient at a stimulation frequency;

measuring the temperature in the interior of said patient and generating a first temperature signal corresponding thereto having a slope with an operational sign;

measuring the temperature in the region of the periphery of said patient and generating a second temperature signal corresponding thereto having a slope with an operational sign;

identifying the operational sign of the slope of at least one of said first and second temperature signals;

determining the difference between said first and second temperature signals, said difference having a normal value;

determining whether said difference upwardly or downwardly transgresses said normal value; and modifying said stimulation frequency based on said operational sign of the slope of said at least one of said first and second temperature signals and on whether said difference upwardly or downwardly transgresses said normal value.

27. A method as claimed in claim 26, wherein the step of measuring the temperature in the interior of said patient is further defined as measuring the temperature of the venous blood of said patient.

28. A method as claimed in claim 27, wherein the step of measuring the temperature of the venous blood of said patient is further defined as measuring the temperature of the venous blood in the right ventricle of said patient.

29. A heart pacemaker comprising:

a housing;

means for stimulating heart activity in said patient at a stimulation frequency;

first sensor means for measuring the temperature at a location in the interior of said patient remote from said housing and generating a first temperature signal corresponding thereto, said first sensor means including a lead extending from said housing to said remote location;

second sensor means mounted in said housing for measuring the temperature in the region of the periphery of said patient and generating a second temperature signal corresponding thereto; and means connected to said means for stimulating and to said first and second sensor means for modifying said stimulation frequency to adapt said stimulation frequency to the physical activity level of the patient including means for determining a chronological sequence of changes respectively occurring in said first and second temperature signals for use as a basis for modifying said stimulation frequency.

30. A heart pacemaker as claimed in claim 29, wherein said means for stimulating heart activity includes an electrode disposed in the right ventricle of said heart of said patient, wherein said first sensor means includes a blood temperature sensor disposed in said right ventricle having an electrical connection via said lead to an interior of said housing, and wherein said electrode is electrically connected to said means for stimulating via said lead of said first sensor means.

31. A heart pacemaker as claimed in claim 30, wherein said means for stimulating heart activity includes an electrode disposed in the right ventricle of said heart of said patient, wherein said first sensor means includes a blood temperature sensor disposed in aid right ventricle having electrical connection via said lead to an interior of said housing, and wherein said electrode is electrically connected to said means for stimulating via said lead of said first sensor means.

32. A heart pacemaker comprising:

a housing;

means for stimulating heart activity in a patient at a stimulation frequency;

first sensor means for measuring the temperature at a location in the interior of said patient remote from said housing and generating a first temperature signal corresponding thereto, said first temperature signal having a slope with an operational sign;

second sensor means disposed in said housing for measuring the temperature in the region of the periphery of said patient and generating a second temperature signal corresponding thereto, said second temperature signal having a slope with an operational sign; and means connected to said means for stimulating and to said first and second sensor means for modifying said stimulation frequency to adapt said stimulation frequency to the physical activity level of said patient, including means for identifying the operational sign of the slope of at least one of said first and second temperature signals for use as a basis for modifying said stimulation intensity and including means for determining the difference between said first and second temperature signals and for determining whether said difference upwardly or downwardly transgresses a normal value of said difference for use as a further basis for modifying said stimulation frequency.

33. A heart pacemaker comprising:

a housing having a first wall adapted, when said housing is implanted in a patient, to be facing the interior of said patient and having a second wall adapted to be facing the body periphery of said patient;

means for stimulating heart activity in said patient at a stimulation frequency;

first sensor means mounted at said first wall for measuring the temperature in the interior of said patient and generating a first temperature signal corresponding thereto;

second sensor means mounted at said second wall for measuring the temperature in the region of the periphery of said patient and generating a second temperature signal corresponding thereto; and means connected to said means for stimulating and to said first and second sensor means for modifying said stimulation frequency to adapt said stimulation frequency to the physical activity level of said patient, including means for determining a chronological sequence of changes respectively occurring in said first and second temperature signals for use as a basis for modifying said stimulation frequency.

34. A heart pacemaker comprising:

a housing having a first wall adapted, when said housing is implanted in a patient, to be facing the interior of said patient and having a second wall adapted to be facing the body periphery of said patient;

means for stimulating heart activity in said patient at a stimulation frequency;

first sensor means mounted at said first wall for measuring the temperature in the interior of said patient and generating a first temperature signal corresponding thereto, said first temperature signal having a slope with an operational sign;

second sensor means mounted at said second wall for measuring the temperature in the region of periphery of said patient and generating a second temperature signal corresponding thereto, said second temperature signal having a slope with an operational sign; and means connected to said means for stimulating and to said first and second sensor means for modifying said stimulation frequency to adapt said stimulation frequency to the physical activity level of said patient, including means for identifying the operational sign of the slope of at least one of said first and second temperature signals for use as a basis for modifying said stimulation frequency and including means for determining the difference between said first and second temperature signals and for determining whether said difference upwardly or downwardly transgresses a normal value of said different for use as a further basis for modifying said stimulation intensity.

* * * * *